United States Patent [19]
Cheng

[11] Patent Number: 5,480,708
[45] Date of Patent: Jan. 2, 1996

[54] CONFORMABLE ORTHOPEDIC CASTING TAPE

[75] Inventor: Peiwen Cheng, Raynham, Mass.

[73] Assignee: Johnson & Johnson Professional, Inc., Raynham, Mass.

[21] Appl. No.: 379,387

[22] Filed: Jan. 27, 1995

[51] Int. Cl.$^6$ ............................... A61F 5/01; B32B 5/04; B32B 5/08; B32B 5/20; B32B 25/08

[52] U.S. Cl. ..................... 428/231; 428/254; 428/542.8; 602/8

[58] Field of Search ................................ 428/231, 254, 428/542.8; 602/8

[56] References Cited

U.S. PATENT DOCUMENTS

| | | |
|---|---|---|
| 3,037,954 | 6/1962 | Gessler et al. . |
| 3,332,416 | 7/1967 | Brickman et al. . |
| 3,758,643 | 9/1973 | Fischer . |
| 4,130,535 | 12/1978 | Coran et al. . |
| 4,668,563 | 5/1987 | Buese et al. ........................ 428/230 |
| 5,256,134 | 10/1993 | Ingham .............................. 428/230 |

*Primary Examiner*—James C. Cannon
*Attorney, Agent, or Firm*—Michael Q. Tatlow

[57] ABSTRACT

A conformable orthopaedic casting tape made with a combination of an elastic fiber and a non-elastic fiber is disclosed. The casting tape is capable of stretching 40% to 200% in the length direction and has a power of between 40 and 175 grams per inch width at 30% elongation. The elastic fiber is a blend of a cured or partially cured polyolefin rubber and a polyolefin resin.

10 Claims, 2 Drawing Sheets

BAR 1     BAR 2     BAR 3

BAR 1     BAR 2     BAR 3

CONFORMABLE ORTHOPEDIC CASTING TAPE

FIELD OF THE INVENTION

The present invention relates to an improved conformable orthopaedic casting tape made with a water reactive polymeric material. The casting tapes of the present invention provide substantial extensibility and elasticity in both their longitudinal and cross direction which results in improved conformability, and thus allows better application of the casting tapes to the patient and the resulting cast better fits or conforms to the patient's limb.

BACKGROUND OF THE INVENTION

Plaster of Paris casts which immobilize body members or limbs have been supplemented and superseded by synthetic casting tapes or bandages which employ water reactive polymeric materials on a substrate. The preferred polymeric materials are water-cured or water-reactive polyurethane prepolymer compositions. The polyurethane materials have largely supplanted other polymeric synthetic casting materials. These polyurethane casting materials are of the type which are disclosed in U.S. Pat. No. 4,376,438 and U.S. Pat. No. 4,411,262.

The fibrous substrate used in the synthetic casting materials is usually a polyester or fiberglass. Although knitted substrates are most common, woven substrates have also been used. The fiberglass materials offer advantages in terms of strength of the finished cast and various constructions of fiberglass fabrics have been used for the substrates for the synthetic casting tapes. The patents mentioned above disclose the use of different fiberglass materials as the substrate for casting tapes. In addition, U.S. Pat. Nos. 3,686,725, 3,787,272 and 3,882,857 disclose specific fiberglass materials, or the treatment of fiberglass yarns, to produce fiberglass substrates which are particularly suitable for use in orthopaedic casts.

U.S. Pat. No. 4,323,061 discloses a cast substrate made from a combination of glass fibers and a second fiber such as cotton, flax, rayon, wool, acrylic resin, nylon, Teflon or polyester. The purpose of the second fiber in the substrate is to hold the curable resin on the substrate.

U.S. Pat. No. 3,332,416 discloses a plaster of Paris cast bandage with a woven substrate made with a combination of elastic and inelastic fibers.

Although fiberglass has been extensively used as a substrate material in orthopaedic casts with different reactive polymers, all of these casting bandages suffer certain disadvantages. One of the major disadvantages is the lack of conformability of the casting tape to the body of the patient. Conformability has been defined as that property which describes the ability of the bandage or casting tape to adapt to or intimately lay down against the compound curves and protrusions of a body member. Fiberglass casting tapes are generally stiffer than casting tapes made of other fibers, and cast technicians and surgeons have some difficulty conforming the fiberglass tapes to the limbs of a patient.

Casting tapes with improved conformability combine elastic and nonelastic yarns in the tape substrate. U.S. Pat. No. 4,668,563 discloses a polyurethane casting tape made from a high modulus fiber such as fiberglass, polyaramide or polyethylene combined with an elastomeric highly extensible fiber made from natural or synthetic rubber or spandex (polyurethane).

U.S. Pat. No. 5,256,134 discloses a polyurethane casting tape containing an elastic yarn such as natural or synthetic rubber or polyurethane and an inelastic yarn formed from polypropylene, polyester, polyamide, polyethylene or cotton or other inelastic natural or synthetic fiber.

A disadvantage of the conformable casting tapes mentioned above is that the elastic fibers employed had serious limitations. As discussed in U.S. Pat. No. 4,668,563, the water reactive polyurethane prepolymer may eventually swell the spandex (polyurethane) filaments causing the filaments to lose their recovery power. The recovery power is the ability of an elastic fiber or filament to recover to its original length after the force applied to stretch the fiber or fabric is released. This loss of recovery power limits the shelf life of conformable casting tapes made with spandex elastic filaments. Natural and synthetic rubber filaments are usually compounded with chemicals which may cause the polyurethane prepolymer to gel prematurely. The premature gelling may be avoided by treating the rubber filaments with an extraction process or by treating the rubber filaments with an acid. Both of these processes are environmentally detrimental and add cost to the substrate and casting tape.

SUMMARY OF THE INVENTION

The present invention provides a highly conformable polyurethane casting tape made with a substrate containing inelastic and elastic yarns which does not have the instability problems or manufacturing problems of previous highly conformable casting tapes. The casting tapes of the present invention use an elastic yarn made from a thermoplastic elastomer which is a blend of an olefin rubber and a thermoplastic olefin resin. These thermoplastic elastomeric blends are referred to as TPEs.

DETAILED DESCRIPTION OF THE INVENTION

Figure 1:
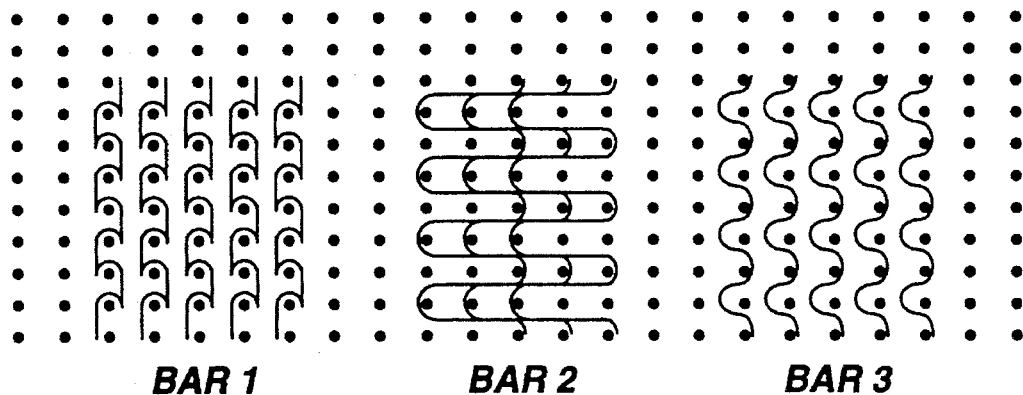
FIG. 1 and FIG. 2 are three bar Raschel knit patterns of the type which can be used in the substrate of the present invention in which bar 1 performs a simple chain stitch and bars 2 and 3 perform lapping motions to lay in yarn.

The substrate of the casting tape of the present invention is constructed i.e. woven or knitted, with a combination of continuous filament high tenacity yarns such as fiberglass yarns or lower tenacity yarns such as polyester yarn or combination of fiberglass and polyester yarns and elastomeric yarns. Fiberglass cast substrates are generally characterized as made from filaments which are sized, formed into yarn, and woven or knitted into the desired structure. The cast substrate fabrics of the present invention are knitted or woven fabrics which combine an inelastic fiber such as fiberglass, polyaramide, polypropylene or polyester with a highly elastic fiber made from a blend of polypropylene and an ethylene propylene rubber. In the present invention the knitted substrates are preferably knitted on a Raschel Warp Knitting Machine having 6 to 28 needles per inch. The terms extensible and extensibility used herein refer to the capability of a material, e.g. fiber or fabric, to stretch without breaking. The term elastic refers to the capability of a material, e.g. fiber or fabric, to recover its size and shape after deformation or stretching.

The elastic fiber is present in a woven or knit fabric in the warp or wale yarns, i.e., machine direction, but normally not in the fill yarns. About 0.25 to 35% of the fibers based on the total weight of fibers in the fabric are extensible. The fabric knitted or woven with elastic yarns has considerable extensibility in the length direction and it is this lengthwise extensibility that provides greater conformability of the resulting casting tape. The extensibility of the fabric of the present invention is at least 40%, and may be as high as 200%, as determined under a static load of 1.5 pounds (680 grams) per inch of width. This also applies to the extensibility of the fabric coated with the prepolymer. The preferred range of extensibility for a knitted fabric is between 60 and 100%. In a woven fabric the elastic fiber is also in the warp yarns, and the fabric should have a stretch in the length direction of up to 200%.

The elastic fiber component of the substrate can be wrapped or unwrapped yarns. The elastic fiber may be wrapped with cotton, nylon or polyester fiber. The elastic fiber or filament may be an extruded filament or it may be a cut thread or filament, i.e. the thread or filament may be cut from a sheet of elastic material. The particular wrapping fiber, if any, is not significant to the present invention.

The substrate contains between 65 and 99.75% by weight, of fiberglass or other yarn and between 0.25 and 35% by weight of the elastic yarn. The substrate preferably contains between 1 and 10% by weight of the elastic yarn. The stretch characteristics of the fabrics can be controlled by the selection of the type of yarn, the number of elastic filaments and the size or gauge of the filaments as well as the tension of the elastic yarns during knitting and the knitting pattern of the fabric.

The elastic yarn provides significant stretch or elasticity of the fabric in the length direction. A typical prior art fiberglass cast substrate has stretch in the length direction of from about 5 to 35%. As stated above, the cast substrates of the present invention have a stretch greater than 40% and up to 200% and a preferred stretch of between 60 and 100%. The substrates will also have some stretch in the cross direction which is the result of the knit pattern structure rather than the presence of the elastic yarns. The cross direction stretch is between about 30 and 80%.

The fabric of the present invention has relatively low power. Power is defined as the force necessary to stretch a fabric a given percentage. It is expressed as force per unit width, e.g. grams/inch width for a specific elongation. The power should be low to prevent constriction of the patient's limb after the tape is applied to the patient and before the prepolymer cures. After the prepolymer is cured, the power of the fabric is not a consideration as the cured polymer will prevent any further constriction. The power of the fabric of the present invention is preferably between 40 and 175 grams per inch width to stretch the fabric 30%. The power of any particular knit fabric construction may be adjusted by changing the thickness or gauge of the elastic yarn. The power may also be adjusted by changing the number of elastic yarns in the fabric or changing the knit construction and by changing the tension of the elastic yarns during knitting. The thermoplastic elastomeric (TPE) thread employed in the present invention has been found to be compatible with the water curable polyurethane prepolymer employed in the casting tape.

The thermoplastic blends of olefin rubber and olefin resins are blends or mixtures of cured or partially cured monoolefin copolymer rubber such as ethylene propylene copolymer rubber ("EPM") or ethylene-propylene non conjugated diene terpolymer rubber ("EPDM") and a polyolefin resin such as polypropylene. Such blends or mixtures are disclosed, for example, in U.S. Pat. Nos. 3,037,954; 3,758,643 and 4,130,535, the disclosures of which are incorporated herein by reference. Generally, the ratio of the rubber to the resin in the blend may vary over a wide range, i.e. from 85% resin (PP) and 15% rubber (EPR) to 25% resin and 75% rubber. The preferred ranges are from 35% to 65% thermoplastic resin and 65% to 35% rubber. In the present invention, the blend should have an ultimate elongation of at least 200%, to be used as an elastic filament or yarn in a casting tape substrate. The composition may also contain up to 300% of an oil-based extender and other conventional rubber compounding ingredients.

The rubber in the mixtures may be partially cured as exemplified by the blends disclosed in U.S. Pat. No. 3,758,643 or fully cured as exemplified by the blends disclosed in U.S. Pat. No. 4,130,535. The blends with the fully cured rubbers are preferred for the present invention. The preferred TPEs are those made from an "insitu" vulcanized olefin rubber and a thermoplastic olefin resin as disclosed in U.S. Pat. No. 4,130,535. These blends are referred to as dynamically vulcanized TPEs.

These blends are unique in that they may be processed into fibers using standard thermoplastic processing equipment yet contain vulcanized rubber which imparts a high degree of resistance to chemical species such as polyurethane prepolymer. This results in a substrate which is particularly suited for casting applications. These dynamically vulcanized TPEs are commercially available under the Tradename SANTOPRENE®. While these polymers are classified as thermoplastic elastomer (TPEs), they behave differently from classical TPEs by virtue of the vulcanized elastomeric component of the blend.

Traditional TPEs are block copolymers composed of alternating "hard" and "soft" segments which phase separate to some degree in the solid state. In this form the "hard" segments serve as crosslinks for the elastomeric soft segments and result in a polymer with bulk properties which resemble vulcanized elastomers. However, when these TPEs are in contact with chemical species which can soften or plasticize the hard segments, the "crosslinks" become weak and the materials lose their elastomeric properties. The polyurethane fiber (SPANDEX) disclosed in U.S. Pat. No. 4,668,563 is believed to be an example of this effect. Although this material could be used to produce acceptable casting tape with conformable properties, the shelf life of the product was less than desirable due to its breakdown of the Spandex fiber by the polyurethane prepolymer. It was found that the prepolymer swelled the Spandex resulting in a softer fiber with unacceptable elastic properties.

U.S. Pat. No. 4,668,563 also disclosed that vulcanized rubber, such as natural rubber can be used for producing acceptable conformable substrates, however, the rubber must first be treated by solvent extraction or with an acid to remove, neutralize or deactivate ingredients present in its composition which lead to premature gelation of the polyurethane prepolymer. Without this treatment the shelf life of a casting tape containing natural rubber would be less than desirable for commercial application.

In order to attain the recovery required for production and performance of a conformable casting tape, the elastomer should have a maximum tension set of 20%, and most preferably below 10%. The hardness of the elastomer, as determined by the Shore hardness index, preferably measured on the Shore A scale, is preferable below 80 and most preferably in the range of 60 and below. Since the elastomer must provide a fabric with low power, the modulus of the elastomer should be low enough so that excessive force is not necessary to stretch it while applying the casting tape to a limb. For this application a 100% modulus of less than 1000 psi is needed, and preferably below 500 psi and most preferably below 300 psi.

Although the ratio of rubber to resin in the blends may vary over a wide range, the blends that are most useful in the present invention are blends of from 35% to 65% thermoplastic polyolefin and from 65% to 35% elastomer. The blends may be selected on the basis of the hardness of the blend and the ability of the material to recover after stretching.

Among the polyurethane prepolymers that can be used as the hardenable resin in the casting tapes of the present invention are those disclosed in U.S. Pat. No. 4,376,438, 4,411,262, and 4,433,680. Other polyurethane prepolymers may also be employed. The cast substrates of the present invention may also be employed with other hardenable resin systems. In the following examples the percent extensibility of a measured piece of elastic fabric is measured at a force of 1.5 pound/inch web width. To determine the crush strength, casting tape with the identical prepolymer is immersed in 75° F. water, squeezing lightly 4 to 5 times under the surface of the water, then wrapped around a 2.75 inch diameter cylinder. The cast is then removed from the cylinder and after a specific time crushed on the crush tester to determine its crush strength. The crush tester applies a force to the cylinder until the cylinder deflects 1 centimeter. The force necessary to cause this deflection is the crush strength.

Figure 2:
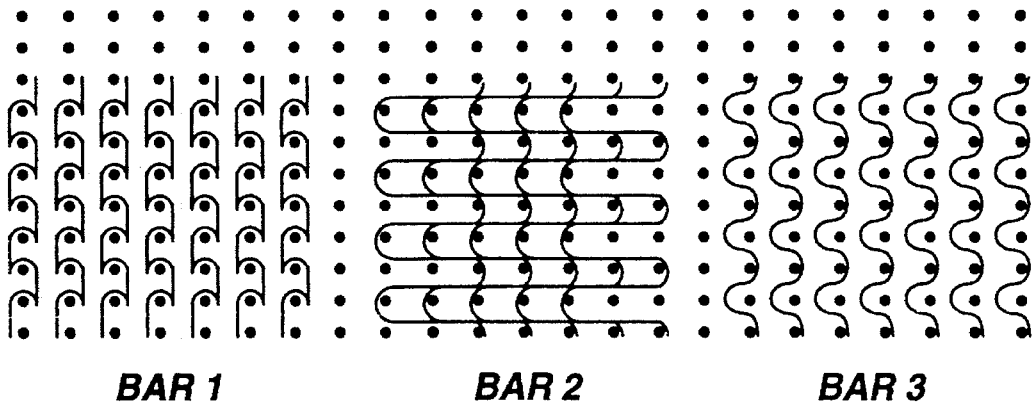

FIG. 1 and FIG. 2 are Raschel knit patterns typical of the type that may be used to manufacture substrates of the present invention. Bar 1 and Bar 2 would be threaded with fiberglass yards and Bar 3 would be threaded with the elastic TPE yarn.

Figure 3:
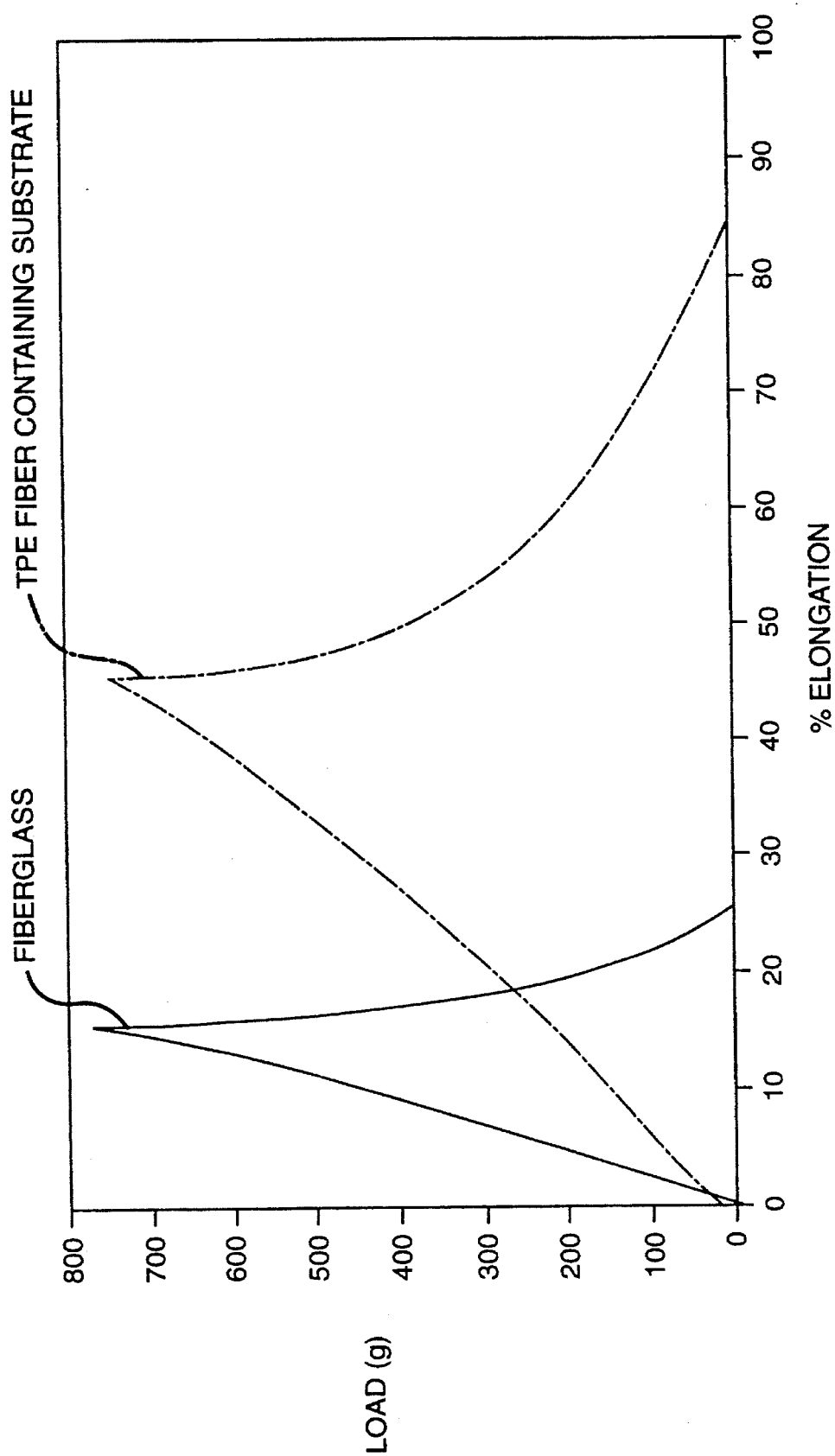
FIG. 3 is an elongation curve of a casting tape containing an elastic fiber as used in the present invention, compared with a fiberglass bandage without elastic fibers.

FIG. 3 shows the difference in elongation between a casting tape substrate which is all fiberglass and a substrate which contains an elastic yarn of the present invention.

EXAMPLE 1

A TPE sold under the trademark SANTOPRENE® 211-45 (with a 45 Shore A hardness) was extruded to make a ribbon consisting of 40 filament ends. The filaments were not subjected to any drawing. The average filament diameter was about 15 mil. Conformable fabric was knitted on a 28-gauge Raschel knitting machine using a three bar configuration shown in FIG. 1. The first and second bars contained DE100 1/0 fiber glass yarn with 60 ends and 57 ends. The third bar contained the 15 mil TPE rubber yarn with 40 ends. The chain link number was:

Bar 1–2,0.0.2;
Bar 2–0,0,0,0;
Bar 3–2,2,0,0;

A 4-inch fabric knitted as above was coated with polyurethane prepolymer to give a cast bandage with 45% prepolymer add-on. The average extensibility after coating was about 60%. The 24 hour crush strength was 122 LB. A cast prepared by applying these bandages to a mannequin leg showed very good conformability; especially over non-uniform areas such as the heal.

EXAMPLE 2

A TPE sold under the name SANTOPRENE® 201-55 with a 55 Shore A hardness, was extruded to make a ribbon consisting of 40 filament ends. The ribbon was then subjected to a 3.5× draw ratio. The average filament diameter was 13.7 mils. The knitting pattern was the same as in Example 1 and was used to make 4 inch fiberglass bandages. The bandages were coated with polyurethane prepolymer to give 45% prepolymer add-on. The extensibility of the bandage after coating was 60%. The crush 24 hour strength was 162 LB. A cast prepared by applying these bandages to a mannequin leg showed very good conformability; especially over nonuniform areas such as the heal.

The following examples illustrate the stability and compatibility of polyurethane prepolymer with the TPE rubber.

EXAMPLE 3

Approximately 10 grams of extruded yarn made from a TPE sold under the designation SANTOPRENE 211-45 was placed in a polypropylene tube containing 30 grams of a polyurethane prepolymer of the type disclosed in Example II of U.S. Pat. No. 4,433,680. The tube was sealed and held at 90° C. in an oven. After 3 days the tube was cooled to room temperature, the prepolymer had not become hard and gelled; i.e., the TPE rubber did not cause premature curing of prepolymer. The prepolymer became hard on the sixth day at 90° C.

EXAMPLE 4

Melt extruded filaments from the dynamically vulcanized TPE SANTOPRENE 211-45, along with two non-chemically crosslinked TPEs tradenamed Lycra T-127, (a polyurethane) and Kraton G-2706 (a styrene-ethylene/butylene-styrene block copolymer) at lengths of 3 inches and 4 inches were stretched to 6 inches length (100% and 50% stretched) and held fixed in place in polypropylene tubes containing 30 grams of polyurethane prepolymer of the type employed in Example 3. The tubes were sealed and aged at 70° C. in an oven. After 3 days the SANTOPRENE threads still remained intact while the Lycra and Kraton had either dissolved or lost their elastic properties completely. The SANTOPRENE sample was cooled to room temperature, and the length was measured. An average 20–25% of stress relaxation was observed and the rubber elastic properties of the threads was maintained. An acid treated natural rubber control showed the same behavior as the SANTOPRENE sample.

EXAMPLE 5

A conformable fabric containing an elastic yarn sold under the designation SANTOPRENE 211-45 was prepared according to Example 1, and coated with a water curable polyurethane prepolymer of the type disclosed in Example 2 of U.S. Pat. No. 4,433,680. The bandages were packaged in aluminum pouches and placed in ovens at 50° C. and 65° C. to determine their shelf-life through accelerated aging. At predetermined intervals the bandages were analyzed for %NCO, % extensibility and recovery. The % NCO measured after 105 days at 50° C. and 28 days at 65° C. indicated that the bandages had over 2 years of shelf life. Control bandages containing natural rubber yarn which had been treated with HCL as described in U.S. Pat. No. 4,668,563 had hardened after 91 days at 50° C. and 24 days at 65° C. The data for % NCO, extensibility and recovery are shown in Tables I and II.

TABLE I

Accelerated Aging Data at 65° C.

TPE

| | Days at 65° C. | | | | |
|---|---|---|---|---|---|
| | 0 | 3 | 9 | 17 | 28 |
| % NCO | 12.30 | 12.05 | 11.72 | 11.09 | 10.80 |
| % Extensibility | 62.5 | 57.5 | 55.6 | 57.5 | 55.0 |
| % Recovery | 100 | 98.8 | 98.4 | 97.3 | 91.2 |

Acid Treated Natural Rubber

| | Days at 65° C. | | | | |
|---|---|---|---|---|---|
| | 0 | 3 | 9 | 17 | 24 |
| % NCO | 12.84 | 12.47 | 11.35 | 10.72 | gelled |
| % Extensibility | 58.9 | 61 | 57.5 | 45.8 | gelled |
| % Recovery | 98.1 | 98.6 | 98.4 | 82.7 | gelled |

TABLE II

Accelerated Aging Data at 50° C.

TPE

| | Days at 50° C. | | | | | |
|---|---|---|---|---|---|---|
| | 0 | 3 | 21 | 49 | 77 | 105 |
| % NCO | 12.30 | 12.25 | 12.44 | 11.85 | 10.93 | 10.83 |
| % Extensibility | 62.5 | 57.0 | 58.2 | 56.8 | 57.4 | 50.2 |
| % Recovery | 100 | 99.6 | 97.7 | 97.8 | 95.5 | 88.3 |

Acid Treated Natural Rubber

| | Days at 50° C. | | | | | |
|---|---|---|---|---|---|---|
| | 0 | 3 | 21 | 49 | 77 | 91 |
| % NCO | 12.84 | 12.88 | 12.48 | 11.52 | 9.98 | gelled |
| % Extensibility | 58.9 | 60.1 | 58.9 | 56.8 | 46.3 | gelled |
| % Recovery | 98.1 | 98.9 | 97.8 | 95.3 | 79.9 | gelled |

EXAMPLE 6

Casting bandages were made using the fabric shown in Example 1 and with a fabric containing acid treated natural rubber as disclosed in U.S. Pat. No. 4,663,563. The polyurethane prepolymer described in U.S. Pat. No. 4,433,680 were coated on the fabric at an add-on 45%. The bandages were dipped in water to activate the prepolymer and the crush strength were measured as previously described. The results of the crush test, force in pounds, are shown in Table 2.

TABLE III

| 15 MIN | 1 HOUR | 24 HOUR | WEIGHT (Grams) |
|---|---|---|---|
| TPE | | | |
| 69.16 | 98.63 | 121.93 | 65.42 |
| NATURAL RUBBER | | | |
| 55.44 | 83.69 | 107.10 | 60.02 |

We claim:

1. An orthopaedic casting tape containing a fibrous substrate impregnated with a water-reactive polyurethane prepolymer, said substrate comprising a combination of an inelastic fiber and an elastomeric fiber which is not substantially reactive with the prepolymer and which will maintain its elastic properties for at least 12 months in contact with the prepolymer, the elastomeric fiber being incorporated in the substrate in the length direction of the substrate to give the substrate an extensibility of between 40% and 200% in the length direction, said substrate having a power such that the force necessary to extend the substrate to 30% elongation is between 40 and 175 grams per inch of substrate width the elastomeric fiber comprising a blend of a cured olefin rubber and an olefin resin which has a Shore A hardness of less than 80 a 100% tensile module of less than 1000 PSI and an elongation of at least 200%.

2. The casting tape of Claim 1 in which the inelastic fiber comprises 99.75%–65.00% by weight of the fiber in the substrate and the elastomeric fiber comprises 0.25 to 35% by weight of the fibers in the substrate.

3. The casting tape of Claim 1 in which the substrate has an extensibility in the length direction of between 60 and 100% under a static load of 680 grams per inch of width.

4. The casting tape of Claim 1 in which the substrate is a Raschel knit fabric.

5. The casting tape of Claim 1 in which the inelastic fiber is fiberglass.

6. The casting tape of Claim 1 in which the substrate is a 3 bar Raschel knit fabric and the elastomeric fiber is in bar 3 of the substrate.

7. The casting tape of Claim 1 in which the inelastic fiber is high tenacity polyester.

8. The casting tape of claim 1 in which the elastomeric fiber is composed of a dynamically vulcanized thermoplastic elastomeric blend.

9. The casting tape of Claim 1 in which the elastomeric fiber is a dynamically vulcanized blend of ethylene propylene rubber and polypropylene resin.

10. The casting tape of Claim 1 in which the elastomeric fiber has a Shore A hardness of less than 60.

* * * * *